United States Patent [19]
Monroe et al.

[11] Patent Number: 5,885,214
[45] Date of Patent: Mar. 23, 1999

[54] INTEGRATED VIDEO DIAGNOSTIC CENTER

[75] Inventors: Richard A. Monroe, Liverpool; Gregory E. Pasik, Auburn; Robert J. Wood, Syracuse; Kevin M. Corcoran, Fayetteville, all of N.Y.

[73] Assignee: Welch Allyn, Inc., Skaneateles Falls, N.Y.

[21] Appl. No.: 802,338

[22] Filed: Feb. 11, 1997

Related U.S. Application Data

[60] Provisional application No. 60/011,558 Feb. 13, 1996.

[51] Int. Cl.$^6$ ........................................... A61B 1/00
[52] U.S. Cl. ..................... 600/407; 600/112; 600/200; 348/77; 348/78
[58] Field of Search ............................... 128/653.1, 897, 128/920; 600/109, 112, 200, 407; 348/65, 77, 68, 69, 72, 75, 78

[56] References Cited

U.S. PATENT DOCUMENTS

| | | |
|---|---|---|
| 4,621,618 | 11/1986 | Omagari . |
| 4,854,302 | 8/1989 | Allfred, III . |
| 4,991,091 | 2/1991 | Allen . |
| 5,181,521 | 1/1993 | Lemelson . |
| 5,239,984 | 8/1993 | Cane et al. . |
| 5,311,859 | 5/1994 | Monroe et al. . |
| 5,331,949 | 7/1994 | Funakoshi et al. . |
| 5,363,839 | 11/1994 | Lankford . |
| 5,373,317 | 12/1994 | Salvati et al. . |
| 5,415,167 | 5/1995 | Wilk . |
| 5,487,661 | 1/1996 | Peithman .................................. 433/29 |
| 5,527,261 | 6/1996 | Monroe et al. .......................... 600/109 |
| 5,527,262 | 6/1996 | Monroe et al. .......................... 600/110 |
| 5,528,323 | 6/1996 | Fujieda et al. . |
| 5,599,276 | 2/1997 | Hauptli et al. .......................... 600/112 |
| 5,630,664 | 5/1997 | Farrelly . |
| 5,701,904 | 12/1997 | Simmons et al. . |
| 5,714,832 | 2/1998 | Shirrod et al. . |

*Primary Examiner*—Marvin M. Lateef
*Assistant Examiner*—Shawna J Shaw
*Attorney, Agent, or Firm*—Wall Marjama Bilinski & Burr

[57] ABSTRACT

An apparatus for medical inspection comprising a hand-held medical diagnostic instrument having a battery pack for providing energy to a light source for illuminating the target area, a housing, a charger for charger the battery pack that is integral with the housing and adapted to provide electric energy to the battery pack to charge the battery pack, a video adapter detachably coupled to the medical diagnostic instrument, video processing circuitry contained within the housing and an umbilicus for connecting the video adapter to the video processing circuitry.

9 Claims, 6 Drawing Sheets

INTEGRATED VIDEO DIAGNOSTIC CENTER

This application claims the benefit of U.S. Provisional patent application Ser. No. 60/011,558 filed Feb. 13, 1996.

BACKGROUND OF THE INVENTION

1. Field of the Invention

This invention relates generally to medical diagnostic instruments, and more specifically to an apparatus that integrates video diagnostic tools into a single unit.

2. Discussion of the Related Art

There are a number of hand-held diagnostic instruments that are used in the physician's office, such as otoscopes, ophthalmoscopes and scopes to examine the skin surface. Hand-held diagnostic instruments typically are equipped with a rechargeable battery pack which can be integrated into the handle of the instrument. The battery pack is recharged using transformers which may either be within a base unit in which the battery pack rests or the battery pack may be configured to plug directly into a standard electrical outlet.

The use of video technology with medical diagnostic instruments is known in the art and has applications with a number of medical instruments, including otoscopes, ophthalmoscopes and the like. Hitachi and Circon offered such products since the early 1980's. These products included a video adapter unit with a CCD imager which could be connected to a hand-held instrument. The video adapter provides the physician with a video display of the target area. The patient and the physician's assistants or students can also view the monitor while the examination is taking place. The technology also provides a means to obtain a video record of the examination. The eletronic data that comprises the video image may also be transmitted to remote locations to facilitate telemedical procedures via modem, satellite transmission or other suitable electronic data transmission methods.

The examination room of a modern day physician contains many various pieces of equipment and assorted medical supplies. The number and complexity of the equipment is increasing. New technologies are providing the medical team with better tools. However, a need exists to maintain an organized and efficient working area in order to allow the physician to make a correct diagnosis and to provide competent medical treatment. In a medical emergency, diagnostic and treatment tools need to be easily and quickly accessible to the medical team.

The complexity of the medical office is compounded by the fact that the various instruments are housed in separate units. In the past, the battery packs of the instruments were charged either in their own holder having a charger therein or were plugged into an electrical outlet. The video processing circuitry was housed in a separate unit. In addition, the video monitor was housed in yet another unit. The medical examination room had a plethora of electrical cords, charging units, and video monitors scattered about which could cause confusion while the physician was attempting to conduct an examination, interfering with the physician's ability to make a quick and accurate diagnosis.

OBJECTS AND SUMMARY OF THE INVENTION

It is therefore an object of the invention to provide a compact storage unit for video inspection equipment for use in a medical examination room.

It is another object of the invention to combine a hand-held medical diagnostic instrument battery pack recharging unit with a video diagnostic unit in a convenient central storage unit.

These objects are obtained by an apparatus for medical inspection comprising a hand-held medical diagnostic instrument having a battery pack for providing energy to a light source for illuminating the target area, a housing, means for charging the battery pack that are integral with the housing and adapted to provide electric energy to the battery pack to charge the battery pack, a video adapter detachably coupled to the medical diagnostic instrument, video processing circuitry contained within the housing and an umbilicus for connecting the video adapter to the video processing circuitry.

BRIEF DESCRIPTION OF THE DRAWINGS

For a fuller understanding of the nature and objects of the invention, reference should be made to the following detailed description of a preferred mode of practicing the invention, read in connection with the accompanying drawings, in which.

DETAILED DESCRIPTION OF THE INVENTION

Figure 1:
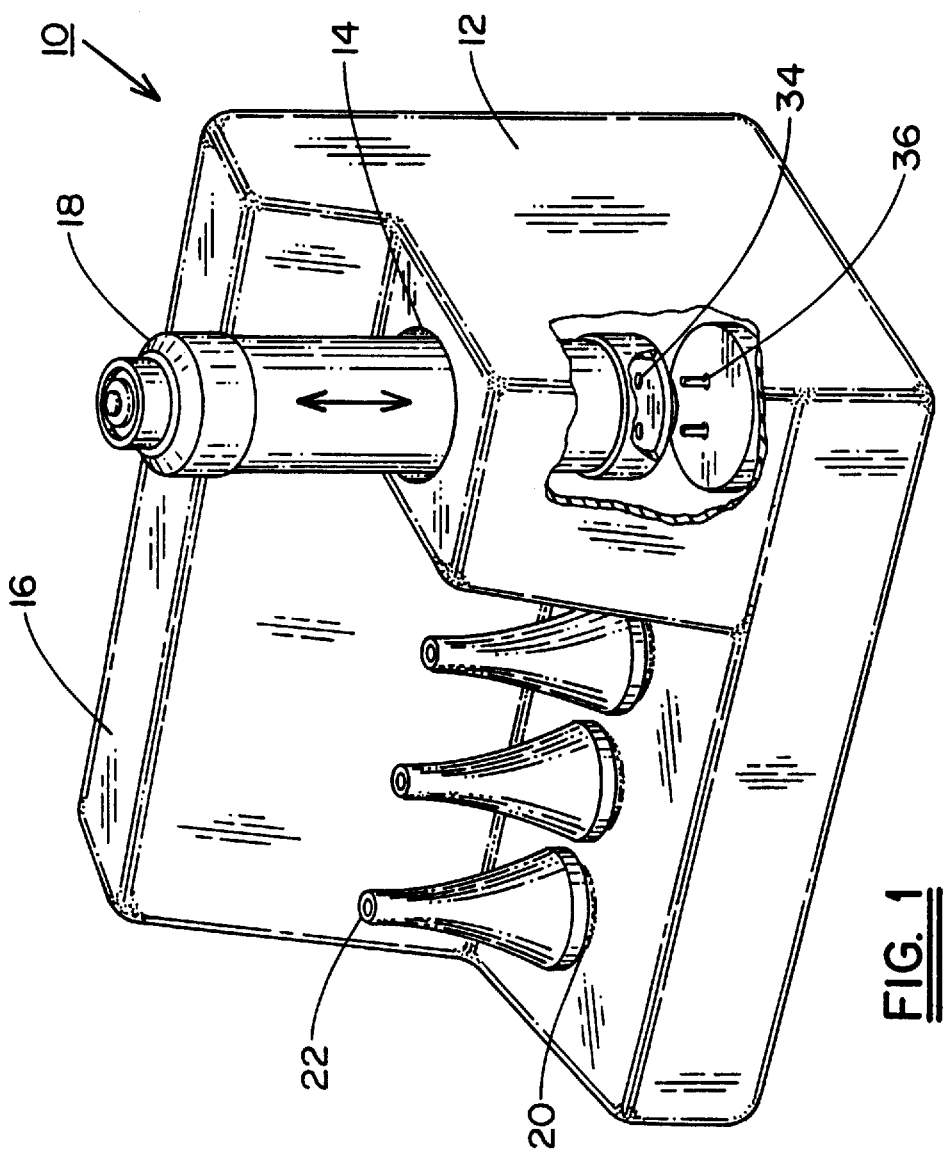
FIG. 1 is a perspective view according to one embodiment of the present invention.

Referring to FIG. 1, there is shown an integrated video diagnostic center embodying the teachings of the invention. The unit 10 has a housing 12 that is suitable for wall mounting; however it is understood that the unit may be placed on a table, or mounted on a roll-around cart, or the unit may be attached to a wall in a boom mount configuration. Preferably the housing 12 is constructed of hard plastic or a similar material. The housing 12 has a recess 14 formed into the top surface 16. In the preferred embodiment, the recess 14 is substantially cylindrical in shape in order to accommodate and provide a cradle for a rechargeable battery pack 18 of the type which is used with a hand-held medical diagnostic instrument, such as an otoscope, ophthalmoscope or the like wherein the battery pack also serves as the handle for the instrument. The recess 14 has an electrical connection integrated therein, which will be explained in greater detail below. The housing 12 has formed therein a convenient holder 20 for specula 22 that are used with the instrument. It will be understood that the housing may be formed to provide storage for other accessories such as swabs or currettes.

Figure 2:
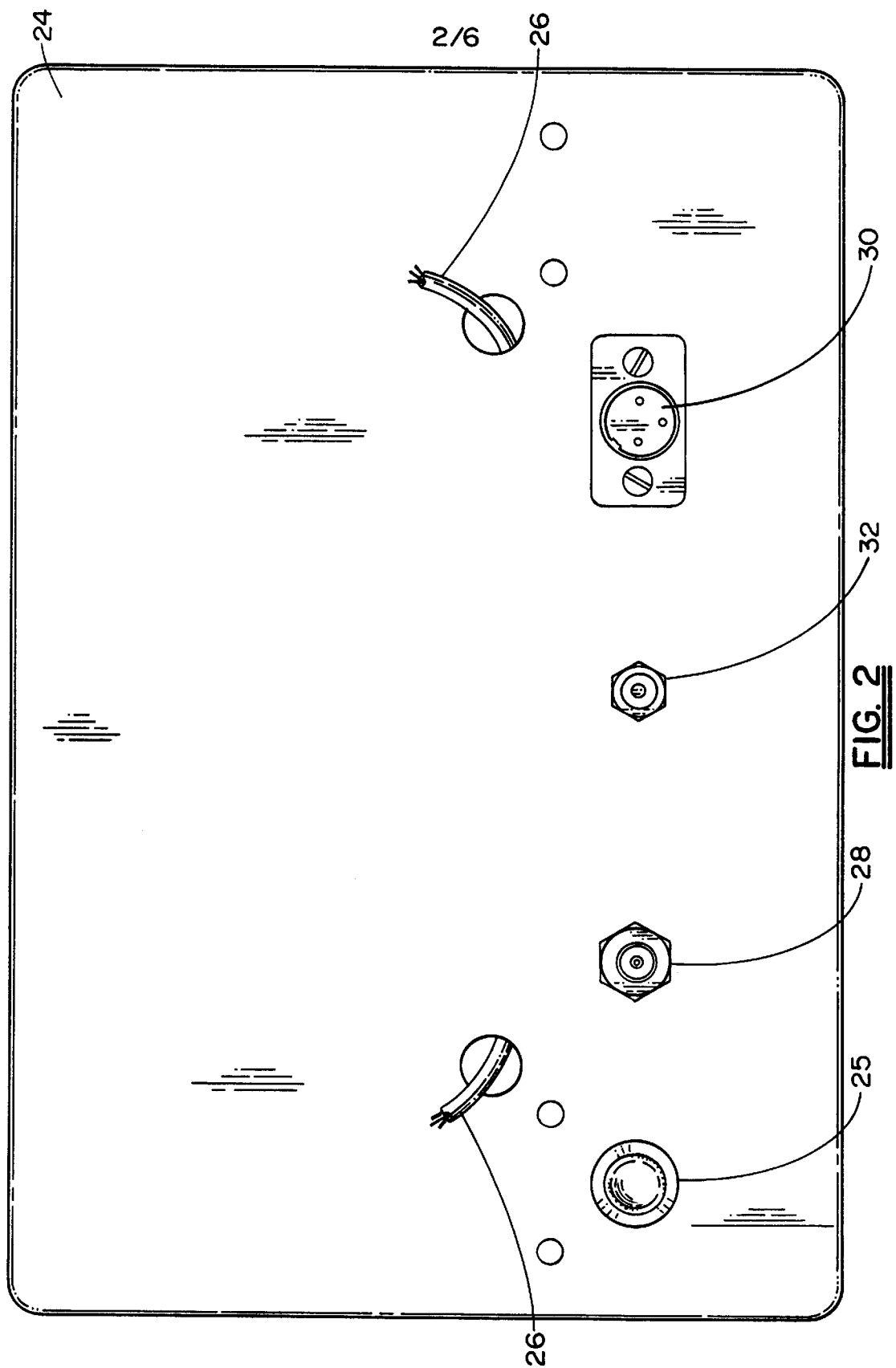
FIG. 2 is a bottom view of the apparatus according to FIG. 1.

Referring to FIG. 2, the bottom face 24 of the unit 10 is depicted. There is an umbilicus 26 that is connected at the distal end to a video adapter 38 (shown in FIG. 4) which connects to a hand-held diagnostic instrument 39. The umbilicus 26 serves to relay the video information from the video adapter 38 to the unit 10. The unit 10 houses electronic video processing circuitry which is well known in the art that processes the video information for suitable use, such as viewing a target area on a video monitor or for transmission of the video data to various data storage instruments (not shown).

The bottom face 24 of the unit 10 also includes a calibration button 25. The user of the apparatus focuses the hand-held diagnostic instrument 39 with the video adapter 38 (FIG. 4) attached onto a suitable calibration surface such as a white sheet of paper. The user depresses the calibration button 25, which when depressed provides an electrical signal to the video processing circuitry, thereby color calibrating the video signal to white. This calibration procedure ensures that any video information transferred to a video monitor or data storage unit is of suitable quality. In addition to performing color calibration, the video processing circuitry may also compensate for back lighting on a video screen. For instance, the hand-held medical instrument, such as an otoscope 39, that is in use with the video adapter 38 may form an image on the video screen that is circular due to the viewing area of the instrument 39. If the image that is projected onto a video screen is not properly compensated for back lighting, the image blooms on the video screen and is not of suitable quality.

The video processing circuitry calibrates for both color and back lighting when the calibration button 25 is depressed. The video processing circuitry stores and maintains the calibration data in memory, even when the unit is powered down. This feature eliminates the need for the user to calibrate the unit each time the unit is used. Of course, one skilled in the art would recognize that the calibration button 25 can be located at any convenient location on the unit 10.

The bottom face 24 of the unit 10 also has a video output connection 28. The video output connection 28 relays information from the video processing circuitry which is contained within the housing 12 to an external monitor or to a video tape machine (not shown). A second video output connection 30 is supplied to provide video information in the Y/C format for external uses. There is also supplied in the bottom face 24 an electrical input connection 32 to provide power to the unit 10. Electrical power from a power source is transformed to provide 2.5 v or 3.5 v to the battery pack recharger as is described below. In addition, electrical power is transformed to provide 12v to the video adapter 38.

Referring again to FIG. 1, the rechargeable battery pack 18 rests in the recess 14. The battery pack 18 is provided with a female coupling 34 to provide contact with the unit 10 by connecting to male coupling 36 which is integral to the unit 10 in order to provide an electric current for recharging. It is understood that there are various configurations capable of performing the recharging of the battery pack 18. For example, a battery recharger may be surface mounted on the housing 12. The hand-held diagnostic instruments include rechargeable batteries to provide power, for example, to operate a light source in the instrument. Typically, the recharging function provides charge at either 2.5 volts or 3.5 volts.

Figure 4:
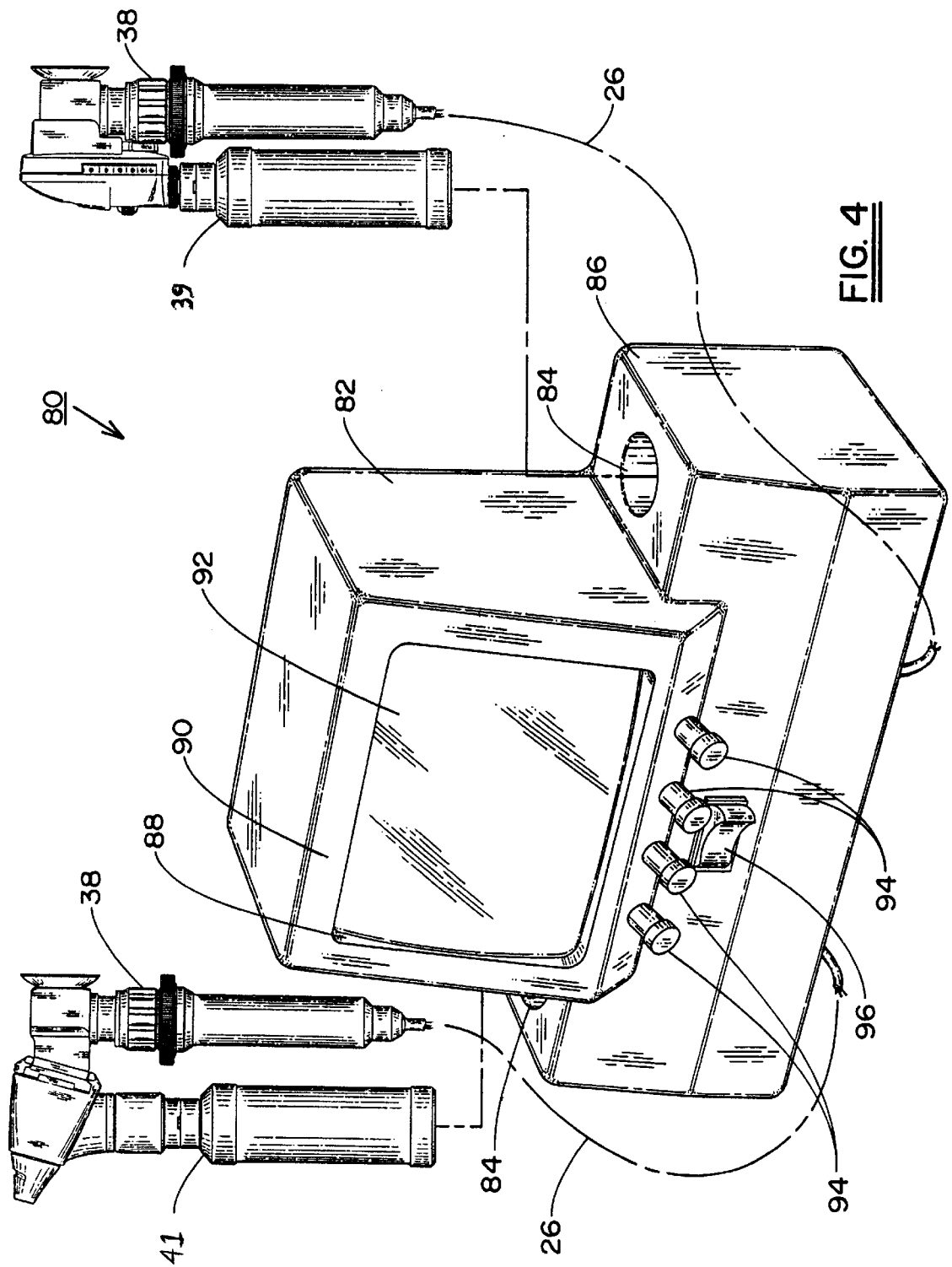
FIG. 4 is a perspective view according to a third embodiment of the invention.

In use, the physician stores the hand-held medical diagnostic instrument in the recess 14 of the housing 12 during which time the battery pack 18 is charged. When the physician performs an examination that requires video technology, the physician removes the battery pack 18, connects the appropriate medical diagnostic instrument to the battery pack 18, and connects the video adapter 38 to the medical instrument 41 (FIG. 4). The physician will have a video monitor 92 in use or the physician may provide the video image to a remote location through telecommunications such as a modem (not shown).

Figure 3:
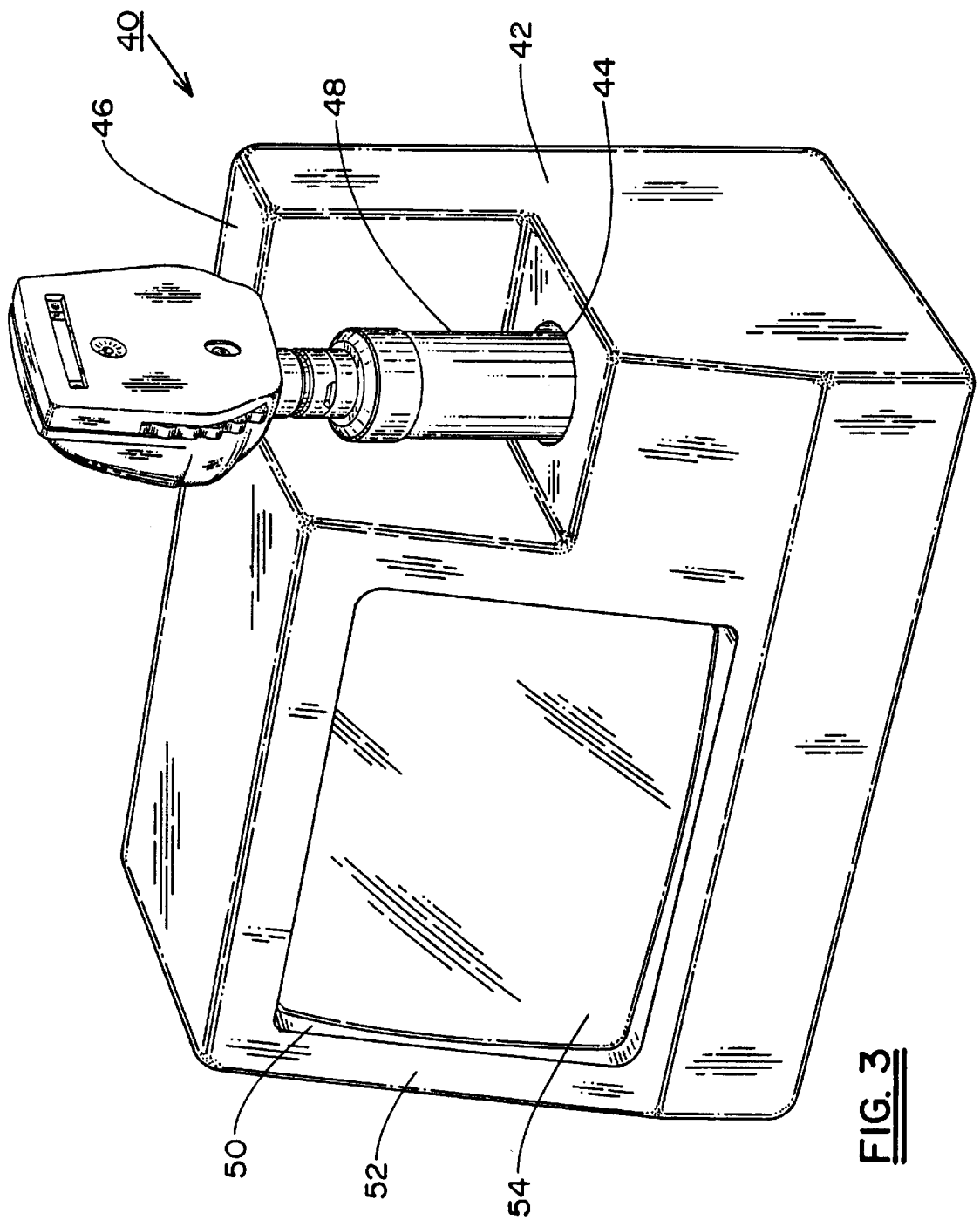
FIG. 3 is a perspective view according to another embodiment of the invention.

Referring now to FIG. 3, there is shown an additional embodiment of the present invention. The unit 40 has a housing 42 that is preferably formed from hard plastic. The housing 42 has a recess 44 in the top surface 46 thereof to accept and cradle a rechargeable battery pack 48 of a hand-held medical diagnostic instrument, in this instance an ophthalmoscope is depicted. The recess 44 provides a connection to the battery pack 48 in order to facilitate recharging, similar to that shown in FIG. 1. An aperture 50 is formed in the front face 52 of the housing 42. The aperture 50 is of sufficient size to accommodate a small video monitor 54, preferably a 5 inch or greater diagonal screen.

The unit 40 provides video output connections, a power supply connection, a calibration button, and an umbilicus connecting the video adapter to the video processing circuitry contained within the housing 42 as shown in FIG. 2. It is understood that the output connections, power supply connection, calibration button and umbilicus may be placed on other faces of the housing 42 to facilitate placement of the unit 40 in the most convenient location. The preferred method is to wall mount the integrated video diagnostic center with the various connections located on the bottom face.

The video information is relayed from the processing circuitry to the video screen 54 where the physician and/or patient can view the target area. This embodiment eliminates the need for a separate monitor in the examination room and thereby achieves the objective of further reducing the number of units in the examination room.

In some instances, the physician may prefer to utilize video adapters with more than one type of hand-held diagnostic instrument, such as an ophthalmoscope and an otoscope, and the embodiment depicted in FIG. 4 provides for the use of two. Of course, a plurality of instruments may be provided for. The unit 80 has a housing 82 preferably formed of hard plastic with two recesses 84—84 formed therein on the top surface 86. The housing 82 has an aperture 88 formed in the front face 90. A video monitor screen 92 is located in the aperture to provide the physician and patient with a view of the target area. There are also standard video control knobs 94 on the front face 90 of the unit 80 to allow the user to tune the monitor 92 to the desired picture quality as is known in the art. The unit 80 has a three-way toggle switch 96 placed in the front face 90, the functionality of which will be described below.

Figure 5:
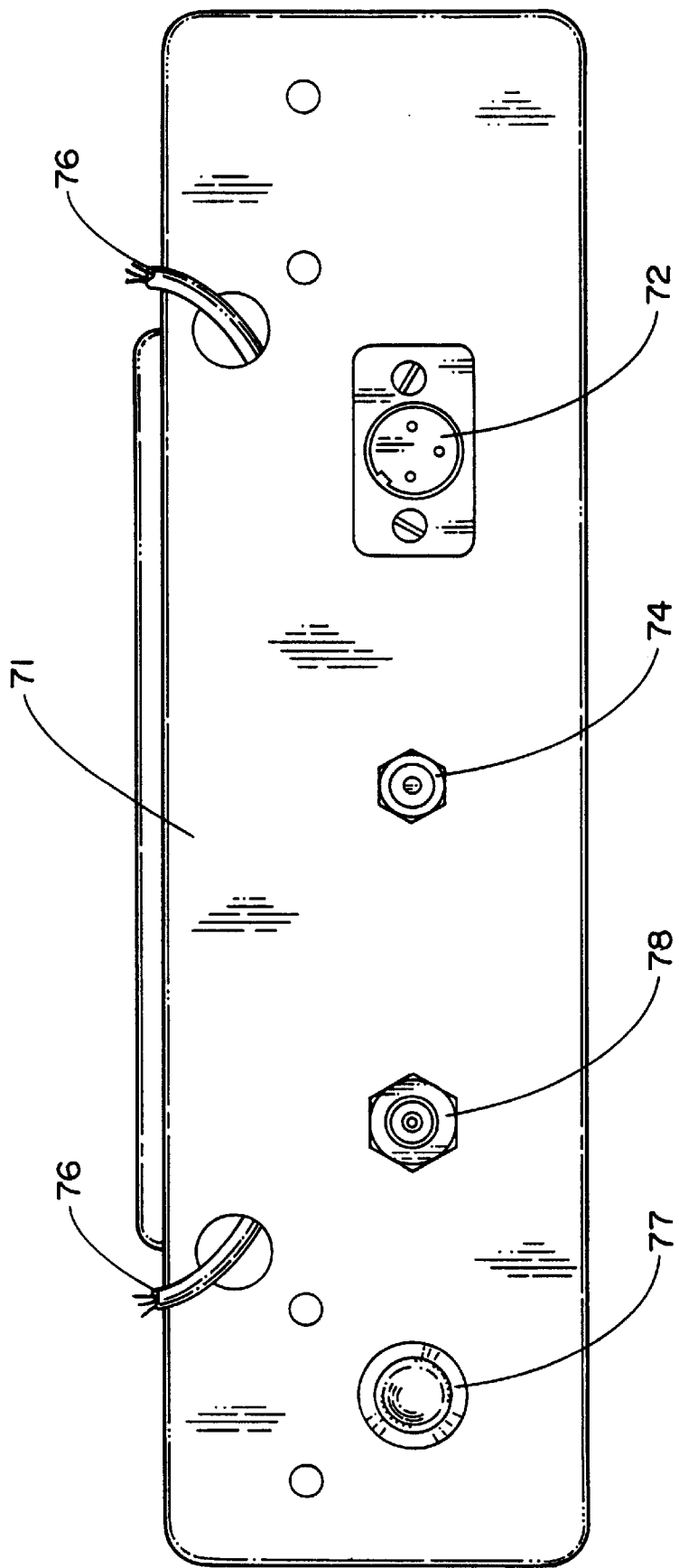
FIG. 5 is a bottom view of the apparatus according to FIG. 4.
Figure 6:
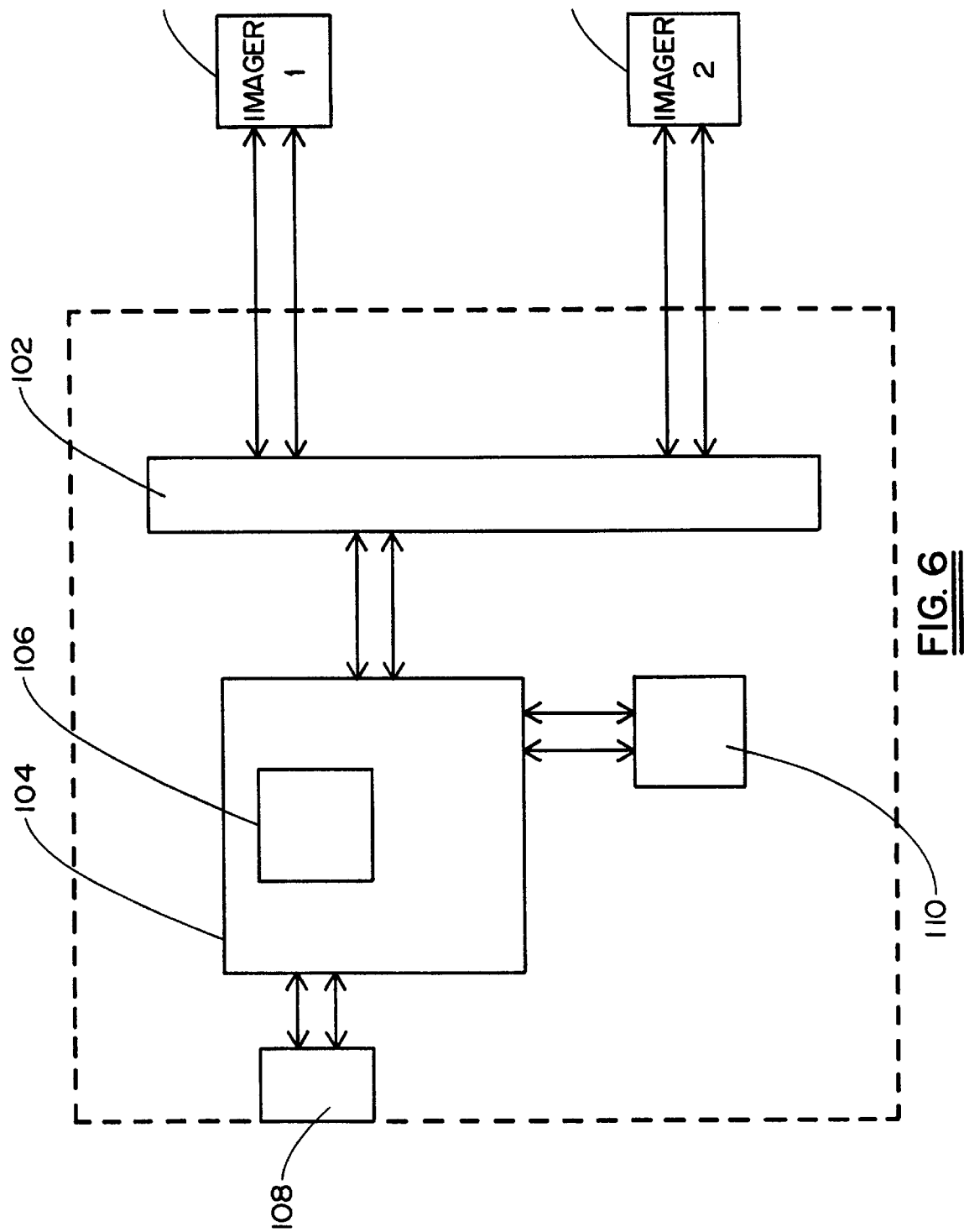
FIG. 6 is a block circuit diagram of one embodiment of the invention.

Referring now to FIGS. 4, 5 and 6, the unit 80 and the bottom face 71 of unit 80 are depicted. The unit 80 provides a coaxial video output connection 78, a Y/C video output connection 72, a power supply connection 74 and two umbilica 76—76 connecting each video adapter 38—38 to the system bus video processing circuitry 102 contained within the housing 82. When the physician selects the middle position on the switch 96, the video unit is inoperative. A selection of the right or left position on the switch 96 determines which of the respective video adapters 38 is operative.

There is a calibration button 77 located on the bottom face 71 of the unit 80. As described above, the calibration button 77, when depressed by the user, sends an electrical signal to the video processing circuitry (FIG. 6). As depicted in FIGS. 4, 5, & 6, the unit 80 has two umbilica 76—76 leading to video adapters 38—38 attached thereto which are controlled by the switch 96. The calibration button 77 operates to calibrate the particular video adapter which has been selected by the positioning of the switch 96. The calibration information for the particular video adapter selected by the switch 96 is stored in the non-volatile memory of the video processing circuitry. Each of the video adapters can be separately calibrated and the calibration information for each is stored in the video processing circuitry in non-volatile memory. Once each video adapter is calibrated, the user need not recalibrate when switching from one adapter to the other because calibration information relating to each adapter is maintained in memory and the video processing circuitry is adapted to utilize memory depending upon the location of the switch 96.

Referring now to FIG. 6, there is shown a block diagram of the video processing circuitry. The imagers 112 and 114 contained within the video adapters 38–38 relay information to the system bus 102 located within the housing (indicated by dashed line in FIG. 6). The system bus 102 relays the information to the microprocessing system 104 which contains a central processing unit 106. An electronic switch 108, corresponding to mechanical three way switch shown as 96 in FIG. 4, selects which of the two imager signals will be relayed to the monitor circuitry 110 for display on the monitor. The electronic switch 108 also relays calibration data for the appropriate imager from the microprocessing system 104 to the monitor circuitry 110. It is understood by one skilled in the art that there are various circuit configurations to accomplish the objective of displaying one or the other of two incoming video signals to a monitor.

In use, the physician selects which hand-held instrument to use and removes it from the recess 84. The physician then selects the corresponding video adapter 38 and connects an instrument, such as a otoscope 39 or an episcope 41, to the video adapter 38. The three way switch 96 is moved to the corresponding position and the video adapter 38 is activated. The physician then performs the examination utilizing video capabilities. When completed, the three way switch 96 is returned to the center/off position, the video adapter 38 is removed, and the hand-held instrument 39 with the battery pack is returned to the recess 84 for storage and charging.

While this invention has been explained with reference to the structure disclosed herein, it is not confined to the details as set forth. For example, the shape of the housing is shown for illustration purposes. One of ordinary skill in the art will recognize that many housing shapes are possible. Also, the battery pack is shown as being recharged in a recess. One skilled in the art will recognize that the battery pack could be mounted on a recharger on the surface of the housing. This application is intended to cover any modifications and changes as may come within the scope of the following claims.

What is claimed is:

1. An integrated video inspection apparatus, said apparatus comprising:
    a housing including means for supporting at least one hand-held optical diagnostic instrument, said at least one hand-held optical instrument having a contained light source for illuminating a target area and a battery pack for providing energy to the light source;
    at least one video imaging adapter detachably engageable with said at least one diagnostic instrument, said at least one video imaging adapter including a miniature video camera and means for coupling said adapter to said instrument for allowing said at least one optical instrument to be converted into a videoized diagnostic instrument;
    video processing circuitry associated with said at least one video imaging adapter disposed within said housing;
    means for connecting said at least one video imaging adapter to said video processing circuitry, said video processing circuitry including means for calibrating the contained miniature video camera; and
    means disposed in said housing for storing calibration data obtained by said calibration means.

2. Apparatus as recited in claim 1, including means integral to said housing for recharging said battery pack of said at least one instrument.

3. Apparatus as recited in claim 1, wherein said housing includes means for retaining at least two hand-held optical diagnostic instruments and at least two video imaging adapters, each adapter being detachably engageable with one of said instruments, said apparatus further including switching means for selectively operating any of said instruments wherein operation of said switching means automatically utilizes calibration data stored by said storage means relating to the instrument selected.

4. Apparatus as recited in claim 1, including a video monitor integral to said housing.

5. An integrated video inspection apparatus, said apparatus comprising:
    at least two hand-held optical diagnostic instruments, each of said instruments having a light source for illuminating a target area;
    a housing;
    at least two video imaging adapters, each said adapter being detachably engageable with said at least two optical diagnostic instruments and including a miniature video camera and means for coupling to at least one of said optical diagnostic instruments;
    video processing circuitry associated with said housing;
    means for connecting said video imaging adapters to said video processing circuitry; and
    switching means for selectively relaying from any one of said at least two video imaging adapters to said video processing circuitry.

6. Apparatus as recited in claim 5, wherein said housing includes an integral video monitor connected to said switching means for displaying video images captured by any connected instrument.

7. Apparatus as recited in claim 5, including calibration means for calibrating the miniature video camera of said at least two video imaging adapters when engaged with a corresponding optical instrument and storing means for storing calibration data of each instrument calibrated by said calibration means.

8. Apparatus as recited in claim 7, in which said switching means is connected to said storing means to automatically recall calibration data relating to a particular instrument without requiring recalibration when any said instrument is selected.

9. A method of selectively and interchangeably using at least two videoized diagnostic instruments, each of said instruments being supported by a housing having video processing circuitry contained therein, said method comprising the steps of:
    selecting a first videoized instrument;
    calibrating said first instrument for white balance;
    storing calibration data relating to white balance associated with said first instrument in storing means associated with said housing;
    selecting a second videoized instrument;
    calibrating said second instrument for white balancing said selected instrument;
    storing calibration data associated with said second instrument in said storage means; and
    selecting one of said instruments at a later time using switching means provided on said housing, wherein said selecting step automatically utilizes the stored calibration data associated with the selected instrument without need for recalibrating said instrument.

* * * * *